(12) United States Patent
Eck et al.

(10) Patent No.: US 7,003,146 B2
(45) Date of Patent: Feb. 21, 2006

(54) X-RAY EXAMINATION APPARATUS AND METHOD FOR FORMING AN X-RAY IMAGE

(75) Inventors: Kai Eck, Aachen (DE); Norbert Jung, Wuerselen (DE); Hendrik Jan Meulenbrugge, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 556 days.

(21) Appl. No.: 09/838,890

(22) Filed: Apr. 20, 2001

(65) Prior Publication Data

US 2001/0038706 A1    Nov. 8, 2001

(30) Foreign Application Priority Data

Apr. 20, 2000  (DE) ............................... 100 19 955

(51) Int. Cl.
*G06K 9/00*  (2006.01)
(52) U.S. Cl. ............. 382/132; 382/131; 382/260; 382/262; 378/48.8; 378/207
(58) Field of Classification Search ............. 382/128, 382/131, 132, 260, 262; 378/48.8, 207
See application file for complete search history.

(56) References Cited

U.S. PATENT DOCUMENTS

| | | | |
|---|---|---|---|
| 5,617,461 A | 4/1997 | Schreiner | 378/98.5 |
| 5,657,400 A | 8/1997 | Granfors et al. | 382/25.4 |
| 6,415,063 B1 * | 7/2002 | Pourjavid | 382/275 |
| 6,529,622 B1 * | 3/2003 | Pourjavid | 382/149 |

FOREIGN PATENT DOCUMENTS

EP    0981998 A1    3/2000

OTHER PUBLICATIONS

Gonzales et al: "Digital Image Processing", 1992, Addison Wessley, XP002240311.

* cited by examiner

*Primary Examiner*—Andrew W. Johns
*Assistant Examiner*—Patrick Edwards

(57) ABSTRACT

The invention relates to an X-ray examination apparatus and a method for forming an X-ray image by means of a processing unit (2) for the correction of image data. In order to achieve automatic correction of imaging defects that are caused by imperfections in the imaging and processing chain, the processing unit (2) is succeeded by a defect detection unit (3) for the detection of image defects that can be detected on the basis of image parameters that can be extracted from image data acquired during clinical examinations, and is suitable for adapting processing parameters (15–21) that are used in the processing unit (2) in dependence on the detected image defects. For the detection of image defects that are caused notably by defective sensor elements or pixels of the X-ray detector there is provided a filter unit (37) which forms a defect table for defective sensor elements in dependence on a threshold value; on the basis of such a defect table a correction table (20) is formed in the processing unit (2) in order to be applied to the image data.

9 Claims, 3 Drawing Sheets

18 OFFSET CORRECTION RULE
19 GAIN CORRECTION
20 CORRECTION TABLE
21 LUT
22 CALCULATED OFFSET
23 ROF UNIT
24 HISTOGRAM FORMING UNIT

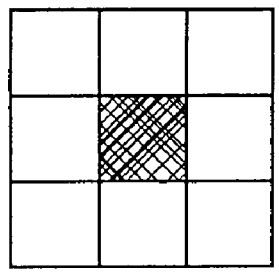
FIG. 4a
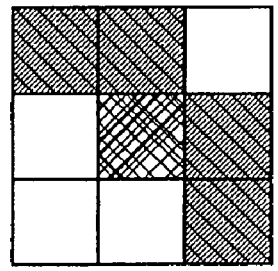
FIG. 4b
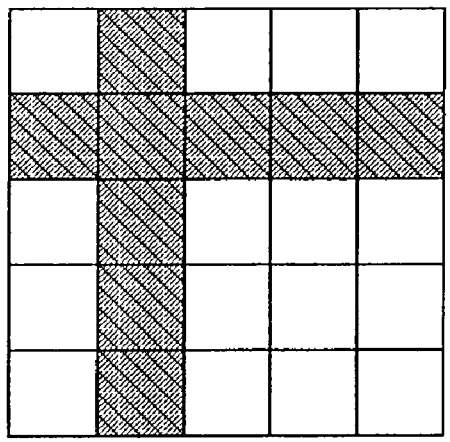
FIG. 4c
FIG. 4d
FIG. 4e

X-RAY EXAMINATION APPARATUS AND METHOD FOR FORMING AN X-RAY IMAGE

FIELD OF THE INVENTION

The invention relates to an X-ray examination apparatus and to a method for forming an X-ray image.

BACKGROUND OF THE INVENTION

U.S. Pat. No. 5,657,400 discloses a method far the correction of bad pixel values of an X-ray detector. A method is described for the identification and correction of defective pixels. For each pixel that is identified as being defective a correction code is stored in a defect table. For the identification a plurality of offset images is acquired first so as to be averaged. Subsequently, a plurality of X-ray images is acquired with a uniform exposure during a special calibration procedure; these images are also averaged. Said two averaged images are subtracted from one another. Defective pixels are determined on the basis of the difference. The calibration procedure is carried out prior to the actual X-ray exposure, without a patient being resent in the X-ray beam path.

The error-free reproduction of X-ray images that is required for diagnostic purposes makes it necessary to correct the image data produced by the X-ray examination apparatus. For example, the geometry of X-ray detectors induces imaging defects that are eliminated by means of correction tables during the image processing. Furthermore, the X-ray detector may involve offset values which are also corrected by way of image processing. During such image processing all imaging defects that are known to the manufacturer are corrected, the image processing then being based only on image parameters that are made available a priori by the manufacturer of the X-ray examination apparatus or on parameters that are obtained by calibration processes performed by means of such X-ray examination apparatus.

However, the range of applications of X-ray examination apparatus is very diverse, so that the loads and effects are different for every X-ray examination apparatus.

Co-operation of a plurality of components is necessary so as to generate an X-ray image, each individual component being subject to an ageing process or to unpredictable environmental influences or loads. Such unpredictable effects have a varying effect on the quality of the X-ray image to be formed.

This type of influencing can be mitigated by periodic updating of correction tables involved in the image processing.

The errors that may occur during the acquisition of X-ray images, however, are not stable in time and not independent either from the relevant mode of operation of the X-ray examination apparatus. A periodic update can be applied so as to ensure a basic quality of the X-ray images acquired by means of the X-ray examination apparatus. However, between the instants at which such a periodic update is carried out there is the risk of overcompensation or undercompensation of image defects or imaging defects and also the risk of occurrence of sudden errors during the acquisition or image processing.

The known method for eliminating imaging defects utilizes image parameters that have not been obtained during the clinical examination. The instantaneous imaging error is not evaluated and a corresponding adaptation method is not determined either.

Therefore, it is an object of the invention to provide an X-ray examination apparatus and a method for forming X-ray images in which imaging defects that are due to imperfections in the image generating and processing chain are automatically corrected.

SUMMARY OF THE INVENTION

This object is achieved by means of an X-ray examination apparatus which includes an X-ray source, an X-ray detector including sensor elements for converting X-ray in electrical charges and a processing unit for the correction of image data and a defect detection unit for the detection of image defects that can be detected on the basis of image parameters that can be extracted from image data arising during clinical examinations and is suitable to adapt, in dependence on the detected image defects, the processing parameters used in the processing unit, whereby for the detection of notably image defects caused by defective sensor elements the defect detection unit includes a filter unit for filtering the image data, and a unit for averaging the filtered image data, and a comparison unit for comparing the filtered and averaged image data with a threshold value in order to form a defect table for the sensor elements in dependence on the threshold value.

The formation of X-ray images of a patient necessitates an X-ray examination apparatus that includes an X-ray source and an X-ray detector. The X-ray detector converts the X-rays whose intensity has been attenuated by the varying thickness of the tissue and the bones of a patient into detectable charge carriers. Such charge carriers are applied to a processing unit by a read-out device. Until this stage of image processing, for example, only a general amplification of the individual image data has taken place. The processing unit converts the coarse image into a form that is suitable for display while using correction tables and interpolation rules. The correction data on which such image processing is based, however, is not adapted to the instantaneous operating conditions of the X-ray examination apparatus. Defects that occur after calibration in the X-ray source or the X-ray detector or in the correction tables are not taken into account.

Therefore, the X-ray examination apparatus in accordance with the invention is based on the evaluation of clinical image data that is derived directly during use of the apparatus. Such clinical image data is extracted during clinical examinations without the apparatus being set in special calibration states. A constant image quality is achieved by continuous detection of image defects.

The processing unit is succeeded by a defect detection unit in which the X-ray images to be formed are subjected to given, appropriate tests so as to detect imaging defects.

To this end, image parameters that are characteristic of the quality of the X-ray image to be evaluated are extracted from the clinical image data. Defect tables or matrices that contain the position of defective pixels or sensor elements are calculated.

In an apparatus in accordance with the invention the clinical image data is filtered in the defect detection unit, notably for the detection of image defects that are caused by defective sensor elements or pixels of the X-ray detector. After the pixel-wise filtering of such image data, the filtered image data is pixel-wise averaged over a plurality of images. The image data thus produced is pixel-wise compared with a threshold value in order to decide whether or not a corresponding pixel value of the pixel considered lies within a predetermined tolerance range. When a pixel value exceeds a threshold value, it is assigned to the pixels designated to be defective. The position of this defective pixel is stored in a defect table. This defect table is used to form a correction table in which a corrected pixel value is assigned to each defective pixel. The correction table is stored in the processing unit, so that the pixels identified as being defective are assigned a corrected pixel value in each subsequent X-ray image. The correction table is replaced, for example, only if the difference between the calculated defect table and the previous defect table lies beyond predetermined tolerance limits.

Ranking filters, notably median filters, are used for the filtering. The inverted original image data is added to the filtered image data. The absolute values of the resultant image data are formed so as to be averaged over a plurality of X-ray images. A pixel value that is representative of each individual pixel of the X-ray detector is thus formed so as to be compared with a threshold value.

This procedure also enables the detection of defective pixels which appear as so-called blinkers in the display, that is, pixels that temporarily have pixel values that are too high and too low.

Median filtering is performed in such a manner that the median of pixel values of a selectable vicinity of the pixel considered is pixel-wise formed.

Depending on the accuracy and the field of application, the filters used are ranking filters (ROF) with a variable kernel size. According to this type of filtering, for example, all pixel values occurring in a square vicinity of the pixel to be filtered are ordered according to rank, a median ROF being the mean pixel value of the representative filter value. As the number of neighboring pixel values to be observed increases, the required amount of calculation work increases but also the quality of the filtering. Customarily, kernel sizes of 3×3 or 5×5 pixels around the pixel observed are used.

The defect recognition in accordance with the invention utilizes exclusively clinical image data. Because of the presence of the patient in the X-ray beam path, the attenuation of the measured signals changes for successive X-ray images. In order to generate, despite such time-variant differences of the attenuation, a defect table which is independent of the image contents, the image data is smoothed and averaged only after the local filtering.

Optionally, a plurality of patient X-ray images with different contents can also be averaged first, followed by filtering. The actual image information would then be attenuated.

The defect table for defective pixels can advantageously also contain indications as regards the temporal validity of the pixel value. It is thus possible that after a predetermined period of time has elapsed, a pixel that has been recognized as being defective is declared to be non-defective again. It is thus achieved that a time-variant pixel defect is not corrected for an indefinite period of time, even though this pixel again yields correct image data. Moreover, the instantaneous information concerning defective pixels can thus be assigned more weight than the previously determined information.

A further possibility consists in renewing the total defect table after a given period of time. Also feasible is defect recognition prior to the processing unit, so that all image data emanating from the X-ray examination apparatus is continuously examined for new defective pixels and a correction is performed each time only for the respective instantaneous X-ray image.

The defect recognition can be applied to the image data of each X-ray image, irrespective of the order in the image processing chain. This requires a large computer capacity. When the defect recognition is performed for every $n^{th}$ image only, it is also possible to use a standard personal computer via an interface.

Information concerning system-dependent pixel defects can be advantageously taken into account for the selection of the ranking filters, so that in the case of defective pixel columns or pixel rows or coherent regions such defects are not taken into account for the defect recognition. The use of such information leads to the application of reduced kernels of the ranking filters. The defective pixel values that are known in advance are then left out from the filtering, so that in the case of, for example, a 5×5 ROF not all twenty-four pixels around the pixel to be evaluated are taken into account for the defect recognition.

However, the fact must then be taken into account that in the case of an excess number of defective pixels in the vicinity of the pixel to be evaluated (which pixels, for example, are then set to zero), this pixel can also be incorrectly evaluated if no lower limit is imposed as regards the number of pixels required for the evaluation; such a lower limit implies, for example, that in the case of less than three non-defective pixels a larger vicinity must be selected for the correction.

This leads to the use of expanded kernels. They enable the expansion of the kernel in the case of, for example, possibly system-imposed defective pixels that are known in advance. The known position of the defective pixel is set to zero and combined according to a logic-AND function by means of a normal ROF. Thus, for the time being a reduced ROF is obtained so as to be supplemented with the number of missing pixels containing information that can be used for the correction, so that an ROF with an expanded kernel is obtained that is adapted to the relevant defect situation. Such supplemented pixels are then situated outside the kernel that is normally arranged as a square around the pixel to be evaluated.

It is an advantageous aspect of the defect recognition in accordance with the invention that the defective pixels are recognized and eliminated without requiring the formation of additional X-ray images or an intervention by medical or technical staff. The defect recognition is based exclusively on image data acquired during the clinical intervention and allows for a robust and reliable defect interpolation and defect reduction during operation of the X-ray examination apparatus, without the availability thereof being reduced.

Because the X-ray detector has different offset images for each individual mode of operation, an offset image must be determined for each mode so as to subtract the offset of the individual sensor elements during the formation of the X-ray image.

To this end, one or more offset images to be averaged are produced by dark imaging prior to each X-ray exposure. The properties of the X-ray detector when not exposed to X-rays are determined on the basis of said dark imaging. This image data for determination of the offset images are gained out of the time of clinical examination.

For the correction of the offset values the test to be performed already exists in the correction, that is, whenever the X-ray detector is not exposed to X-rays a number of dark images are formed at instants that can be fixed; these dark images are averaged and a mean offset table is formed. This table can be used to update the correction rule that is present in the processing unit for the offset correction, updating being continuous or periodical, depending on the work load of the computer and the X-ray examination apparatus.

Such image parameters, mentioned merely by way of example, are compared either with the processing parameters stored and used in the processing unit or with reference values that are stored directly in the defect detection unit and are derived from the previously formed X-ray images.

It has been found that it is advantageous to perform the error detection continuously. The smallest deviations can thus be quickly detected and corrected without requiring a large amount of time, possibly also without an additional radiation load.

It is another advantage of the invention that a correction is performed only when an imaging defect was detected. Computer capacity and time are thus saved.

Because the correction of the processing parameters in the processing unit and/or the status parameters of the X-ray examination apparatus is performed in dependence on the imaging defect detected by the defect detection unit, an X-ray image that has been corrected for imaging defects is applied to the defect detection unit again in which a defect detection is performed once more. When the quality evaluation criteria are within selectable tolerance limits, the X-ray image wherefrom imaging defects have been removed is displayed by means of an output unit.

The detection of a further image defect, or still the same image defect, in an X-ray image after a first adaptation, initiated by the defect detection unit, of the processing parameters or status parameters, is indicative that the already executed adaptation was not adequate. In such a case the defect detection unit will perform a different adaptation. If so permitted by the operating condition of the X-ray examination apparatus, for example, the apparatus is set to a standby mode and a basic calibration is performed. To this end, for example, dark images are acquired and the offset compensation is adapted anew or the user is instructed to make phantom images or to adjust the X-ray examination apparatus in conformity with a rule. When the imaging defect cannot be eliminated by means of the available automatic adaptation methods, a service technician is informed. The technician can interrogate, via a remote link, the status of the X-ray examination apparatus and carry out appropriate adaptations of the exposure criteria or processing parameters.

The objects are also achieved by means of a method of forming X-ray images.

The object is also achieved by means of a computer program for the correction of image data, whereas a correction being performed notably for image defects that are caused by defective sensor elements by forming a defect table for the sensor elements by the filtering of clinical image data by means of ranking filters and by the averaging of the filtered image data and also in dependence on a threshold value.

BRIEF DESCRIPTION OF THE DRAWINGS

An embodiment of the invention will be described in detail hereinafter with reference to the drawings.

Therein:

FIGS. 4a–e show ranking filters.

DETAILED DESCRIPTION OF THE DRAWINGS

Figure 1:
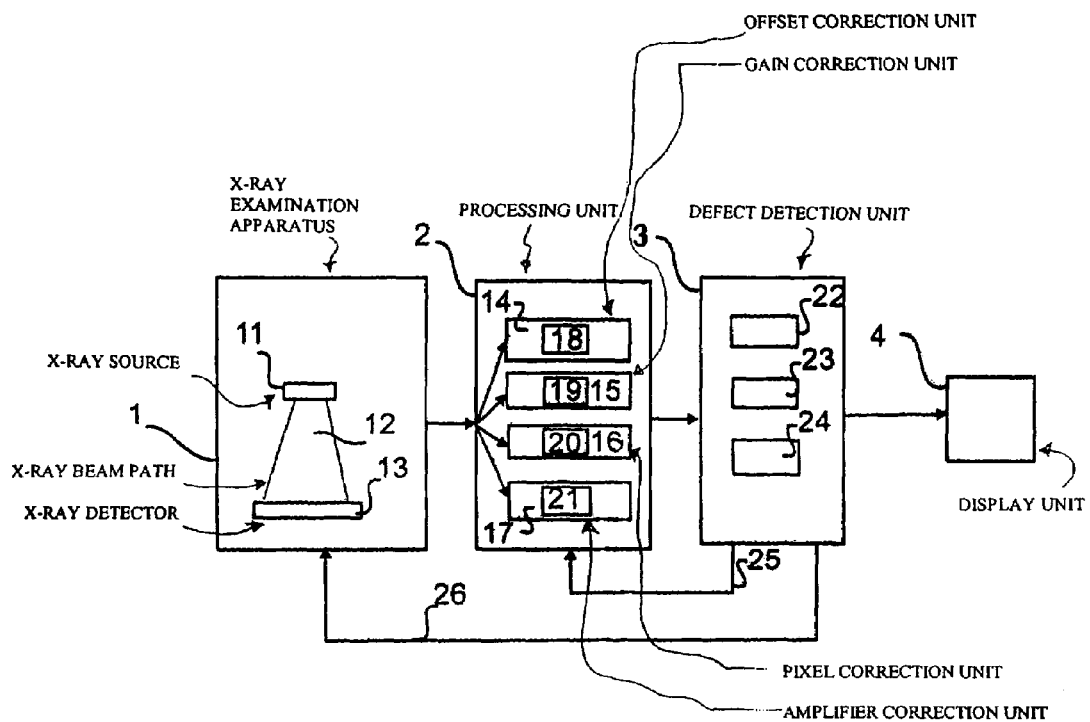
FIG. 1 is a diagrammatic view of an X-ray examination apparatus.

FIG. 1 shows an X-ray examination apparatus which includes an imaging unit 1 that consists of an X-ray source 11, an X-ray beam path 12 and an X-ray detector 13. The imaging unit 1 is succeeded by a processing unit 2 with an offset correction unit 14, utilizing an offset correction unit 18, a gain correction unit 15, utilizing a gain correction factor 19, a correction unit 16 for the correction of defective pixels by means of a correction table 20, and a unit 17 for the correction of non-linear amplifier behavior by means of a look-up table (LUT) 21. The processing unit 2 is succeeded by a defect detection unit 3 in which the X-ray image corrected by the processing unit 2 is scrutinized for any residual image defects.

The offset deviation is corrected by means of dark images. When the newly calculated offset correction rule 22 deviates from the offset correction rule 18, the offset correction rule 18 present in the processing unit 2 is replaced.

The image data emanating from the processing unit is also examined for defective pixels in the ROF unit 23. The ROF unit 23 calculates a defect table which is compared with the defect table on which the correction table 20 in the processing unit is based. In the case of a deviation, the defect table is replaced, and hence also the correction table 20 for the correction of defective pixels.

The unit 24 forms histograms over the pixel values or grey values from the image data for selectable regions of the X-ray detector. A deviation between the curves occurring after subsequent integration of said histograms indicates a non-linear amplifier behavior between, for example, neighboring regions of the X-ray detector that are read out by different amplifier circuits. In the case of deviation a LUT is calculated in order to restore the pixel values that have not been correctly amplified to the correctly amplified pixel values. This LUT is calculated only if a deviation occurs between the curves resulting from the integration of the histograms.

If no deviations occur during these tests, the X-ray image that is free from imaging defects is displayed on the display unit 4.

The LUTs, defect tables and correction tables or offset correction rules are applied to the processing unit 2 via the connection 25. The defect detection unit 3 acts on the image acquisition unit 1 via the connection 26. Such acting takes place when a defect occurs again, despite an update of the relevant rule, so that the X-ray examination apparatus may have to be set to a standby mode or basic settings that are stored in the X-ray detector 13 must be fetched or initialized.

Figure 2:
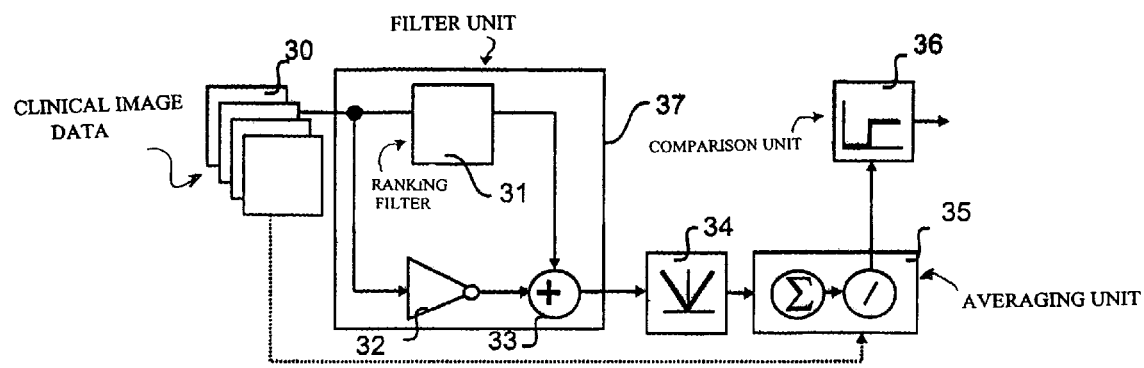
FIG. 2 illustrates defect detection with pixel defect recognition.

FIG. 2 shows the pixel defect recognition in accordance with the invention. The clinical image data 30 is applied to a filter unit 37. The filter unit 37 includes a ranking filter 31, an inverter 32 and a summing unit 33. The inverted original data is added to the filtered image data. The absolute value of the pixels is formed in the unit for forming the absolute value 34 from the intermediate image data thus appearing. These steps are averaged in the averaging unit 35 over a plurality of frames or X-ray images. To this end, the rectified intermediate image data is divided by the number of frames considered. The averaged image data thus obtained is compared with a threshold value in the comparison unit 36. All pixel values that exceed a threshold value are stored in a defect table. The pixels that are identified as being defective in the defect table are corrected by means of the correction table 20 stored in the processing unit and in the processing unit 2 the corrected pixel values are applied to the image data from the X-ray detector 13.

Figure 3:
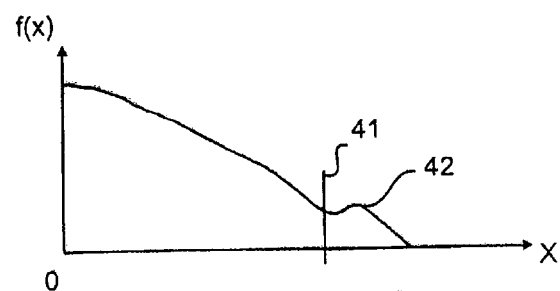
FIG. 3 shows a diagram illustrating the formation of a threshold value.

FIG. 3 shows a diagram which is used to define the threshold value 41. The number of pixels f(x) that deviate from their ideal value continuously decreases in an X-ray detector. The defective pixels exhibit an irregularity 42 in said continuous decrease. Consequently, the threshold value must lie directly ahead of the deviation value at which the defective pixels congregate. Another possibility for defining the threshold value arises when a histogram of the grey values of the pixels occurring is formed subsequent to the unit 34 for forming the absolute value of the filtered and averaged image. A deviation of the normally monotonous variation in this histogram is indicative of the congregation of defective pixels, so that the threshold value can also be determined in this manner. It is also possible to acquire the histogram continuously and hence to define the threshold value in an adaptive manner. This offers the advantage that in the case of a disturbance, that has the same effect on all pixels and leads to pixel values that all exceed the manually preadjusted threshold value, the threshold value is automatically changed and a usable X-ray image is displayed; this would not be so in the case of manual threshold value adjustment.

FIG. 4a shows a ranking filter with a 3×3 kernel. The 3×3 kernel is used for the filtering of the pixel under consideration; that is, during the filtering of a pixel value the pixels and pixel values which neighbor the pixel to be considered are used in a 3×3 environment.

FIG. 4b shows the position of known defective pixels, the central pixel being the pixel to be evaluated.

FIG. 4c shows a reduced ranking filter in which such defective pixels and their known position are taken into account. The defective pixels are then set to zero, so that they are not taken into account for the filtering.

FIG. 4d shows the position of defective pixels in a 5×5 environment. FIG. 4e shows an expanded kernel where normally 9 coefficients are taken into account, but 9 coefficients cannot be used any longer for the filtering because of the defective pixels that are known in advance. In order to avoid this, the missing coefficients are derived from the immediate vicinity, resulting in a ranking filter with an expanded kernel.

The invention claimed is:

1. An X-ray examination apparatus which includes an X-ray source (11),
    an X-ray detector (13) including sensor elements for converting X-ray in electrical charges and a processing unit (2) for the correction of image data and a defect detection unit (3) for the detection of image defects that can be detected on the basis of image parameters that can be extracted from image data arising during clinical examinations and is suitable to adapt, in dependence on the detected image defects, the processing parameters (18–21) used in the processing unit (2), characterized in that for the detection of image defects caused by defective sensor elements the defect detection unit (3) includes
    a filter unit (37) for filtering the image data,
    a unit (35) for averaging the filtered image data,
    a comparison unit (36) for comparing the filtered and averaged image data with a threshold value in order to form a defect table identifying defective pixels in the image data, and
    a processing unit (2) for correcting the defective pixels identified in the defect table by means of a correction table (20) to obtain corrected pixel values and applying the corrected pixel values to the image data from the X-ray detector (13), wherein the correction table (20) is based on a defect table, wherein the defect detection unit (3) calculates a defect table which is compared with the defect table on which the correction table (20) is based, and wherein in the case of a deviation between the two defect tables, the defect table upon which the correction table (20) is based is replaced, as well as the correction table (20) for the correction of defective pixels.

2. An X-ray examination apparatus as claimed in claim 1, characterized in that the defect detection unit (3) is arranged to adapt status parameters of the X-ray examination apparatus.

3. An X-ray examination apparatus as claimed in claim 1, characterized in that continuous detection takes place.

4. An X-ray examination apparatus as claimed in claim 1, characterized in that
    the filter unit (37) includes a ranking filter (31) for filtering the image data, an inverter (32) for inverting image data, and
    a summing unit (33) for summing the filtered and inverted image data, there also being provided a unit (34) for forming the absolute values of the summed image data.

5. An X-ray examination apparatus as claimed in claim 1, characterized in that
    the defect detection unit (3) is arranged to apply a corrected defect table to the processing unit (2) in the case of detection of defective sensor elements.

6. An X-ray examination apparatus as claimed in claim 1, characterized in that
    the threshold value is predetermined or can be defined adaptively by forming histograms of the image data subsequent to the unit (34) for forming the absolute value.

7. An X-ray examination apparatus as claimed in claim 4, characterized in that
    the ranking filter (31) has variable kernels.

8. A method of forming X-ray images with an X-ray examination apparatus as claimed in claim 1.

9. A computer-readable medium for storing a computer program for the correction of image data comprising the steps of forming a defect table identifying defective pixels, and correcting the defective pixels identified in the defect table by means of a correction table (20) to obtain corrected pixel values, and applying the corrected pixel values to the image data wherein the correction table (20) is based on the defect table, wherein a defect detection unit (3) calculates a defect table which is compared with the defect table on which the correction table (20) is based, and wherein in the case of a deviation between the two defect tables, the defect table upon which the correction table (20) is based is replaced, as well as the correction table (20).

* * * * *